United States Patent [19]

Hartman et al.

[11] Patent Number: 5,358,956

[45] Date of Patent: * Oct. 25, 1994

[54] FIBRINOGEN RECEPTOR ANTAGONISTS

[75] Inventors: George D. Hartman; Wasyl Halczenko, both of Lansdale, Pa.

[73] Assignee: Merck & Co., Inc., Rahway, N.J.

[*] Notice: The portion of the term of this patent subsequent to Nov. 23, 2010 has been disclaimed.

[21] Appl. No.: 960,741

[22] Filed: Oct. 14, 1992

[51] Int. Cl.$^5$ ................. A61K 31/445; C07D 211/32
[52] U.S. Cl. ................... 514/331; 514/305; 514/323; 514/326; 514/538; 546/133; 546/201; 546/208; 546/210; 546/232; 546/233; 546/234; 562/430; 562/439; 562/440; 562/442; 562/454
[58] Field of Search .............. 546/133, 201, 232, 210, 546/233, 208, 234; 514/305, 323, 331, 326, 538; 564/85, 86, 88, 90, 237, 244, 337, 364; 562/430, 440, 442, 451, 439

[56] References Cited

U.S. PATENT DOCUMENTS

| | | | |
|---|---|---|---|
| 4,064,255 | 12/1977 | Champseix et al. | 546/201 |
| 4,122,255 | 10/1992 | Krapcho | 544/398 |
| 4,243,807 | 1/1981 | Friebe et al. | 546/232 |
| 4,622,331 | 11/1986 | Jozic | 546/232 |
| 5,030,654 | 7/1991 | Barnish | 546/233 |
| 5,064,814 | 11/1991 | Klien et al. | 530/331 |

FOREIGN PATENT DOCUMENTS

| | | |
|---|---|---|
| 0352249 | 1/1990 | European Pat. Off. |
| 0372486 | 6/1990 | European Pat. Off. |
| 0381033 | 8/1990 | European Pat. Off. |
| 0384362 | 8/1990 | European Pat. Off. |
| 0405537 | 2/1991 | European Pat. Off. |
| 0478328 | 4/1992 | European Pat. Off. |
| 0478362 | 4/1992 | European Pat. Off. |
| 0478363 | 4/1992 | European Pat. Off. |
| 0479481 | 4/1992 | European Pat. Off. |

OTHER PUBLICATIONS

Hartman et al "Nonpeptide fibrinogen receptor autagonist. 1. Discovery and design of exosite inhibitors" J. Med. Chem. 35 4640–4642 (1992).

*Primary Examiner*—Celia Chang
*Attorney, Agent, or Firm*—Richard S. Parr; Mel Winokur; Paul D. Matukaitis

[57] ABSTRACT

Novel fibrinogen receptor antagonists of the formula:

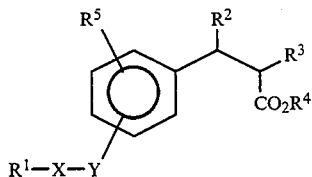

are provided in which the claimed compounds exhibit fibrinogen receptor antagonist activity, inhibit platelet aggregation and are therefore useful in modulating thrombus formation.

8 Claims, No Drawings

FIBRINOGEN RECEPTOR ANTAGONISTS

BACKGROUND OF THE INVENTION

The invention relates generally to modulating cell adhesion and to inhibiting the binding of fibrinogen and other proteins to blood platelets, and inhibiting the aggregation of blood platelets specifically to the platelet IIb/IIIa (gpIIb/IIIa) fibrinogen receptor site. Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothethial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the platelet glycoprotein IIb/IIIa (gpIIb/IIIa) receptor complex.

Attempts have been made to use natural products and synthetic peptides to determine the mechanism of adhesion and platelet aggregation. For example, Rouslahti and Pierschbacher in Science, 238, 491–497 (1987), describe adhesive proteins such as fibronectin, vitronectin, osteopontin, collagens, thrombospondin, fibrinogen, and von Willebrand factor that are present in extracellular matrices and in blood. The proteins contain the tripeptide arginine-glycine-aspartic acid (RGD) as their glycoprotein IIb/IIIa recognition site. These arginine-glycine-aspartic acid-containing tripeptides are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh in Proc. Nat'l Acad. Sci. U.S.A., 84, 6471–6475, (1987), describes an Arg-Gly-Asp directed adhesion receptor expressed by human endothethial cells that is structurally similar to the IIb/IIIa complex on platelets but is antigenically and functionally distinct. This receptor is directly involved in endothelial cell attachment to fibrinogen, von Willebrand factor, and vitronectin.

Pierschbacher and Rouslahti, in J. of Biol. Chem., 262, (36), 17294–17298 (1987) hypothesized that the Arg-Gly-Asp sequence alone would be a sufficient signal for receptor recognition and binding and, therefore, the conformation of the tri-peptide sequence would be determinative. Various synthetic peptides were produced and the authors concluded that the sterochemical conformation of Arg-Gly-Asp as influenced by enantiomeric substitutions or additions to this sequence significantly influenced receptor-ligand interaction. The authors further showed that cyclization of a decapeptide by forming a disulfide bridge between non-terminal residues Pen and Cys, rendered the peptide much less effective at inhibiting attachment to fibronectin.

In Proc. Nat'l Acad. Sci. U.S.A., 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517. A number of large polypeptide fragments in the cell-binding domain of fibronectin have cell-attachment activity. For example, see U.S. Pat. Nos. 4,517,686, 4,661,111 and U.S. Pat. No. 4,578,079.

Ruggeri et al., Proc. Nat'l Acad. Sci. U.S.A., 83, 5708–5712 (1986) explore a series of synthetic peptides designed in lengths to 16 residues, that contain RGD and a valine attached to the aspartic acid residue of RGD that inhibit fibrinogen binding to platelets. See also Koczewiak et al., Biochem. 23, 1767–1774 (1984); Ginsberg et al., J. Biol. Chem. 260(7), 3931–3936 (1985); and Hayerstick et al., Blood 66(4), 946–952 (1985). Other inhibitors are disclosed in Eur. Pat. App. Nos. 275,748 and 298,820.

A number of low molecular weight polypeptide factors have been isolated from snake venom. These factors apparently have high affinity for the gpIIb/IIIa complex. For example, Huang et al., J. Biol Chem., 262, 16157–16163 (1987); Huang et al., Biochemistry 28, 661–666 (1989) describe the primary structure of the venom trigramin which is a 72 amino acid polypeptide that contains the RGD subunit. Echistatin is another venom which has high affinity for the gpIIb/IIIa complex. This polypeptide contains 49 amino acids and has the RGD subunit and various disulfide bridges. Gan et al., J. Biol. Chem., 263, 19827–19832 (1988). See also, Dennis et al., Proc. Nat'l Acad. Sci. USA, 87, 2471–2475 (1989). However, these snake venom factors also have high affinity for other members of the adhesive protein receptor family including the vitronectin and fibronectin receptors so are not selective for the gpIIb/IIIa complex.

While it is known that the tripeptide sequence Arg-Gly-Asp is present in certain polypeptides that can duplicate or inhibit the cell attachment-promoting effects of fibronectin and vitronectin, the tri-peptide Arg-Gly-Asp has low activity. U.S. Pat. No 5,023,233, assigned to Merck & Co., Inc., discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gpIIb/IIIa receptor. U.S. Pat. No. 5,037,808 discloses guanidino peptide mimetic compounds that retain an Asp residue which inhibit platelet aggregation. The application PCT/US90/02746 describes the use of antibody-polypeptide conjugates wherein said polypeptides contain the Arg-Gly-Asp (RGD) sequence.

The application PCT/US91/00564 discloses the use of large cyclic peptides containing RGD flanked by proline residues which are platelet aggregation inhibitors. The application PCT/US90/03788 discloses small cyclic platelet aggregation inhibitors which are synthetic cyclic pentapeptides containing the tripeptide sequence Arg-Gly-Asp and a thioether linkage in the cycle. The application PCT/US90/05367 published May 2, 1991 also discloses the use of peptides and pseudopeptides such as N-amidino-piperidine-3-carboxylglycyl-L-aspartyl-L-valine that inhibit platelet aggregation and thrombus formation in mammalian blood. The application Eur. Pat. App. No. 91103462.7 discloses linear compounds which can include internal piperazinyl or piperidinyl derivatives. Eur. Pat. App. No. 91300179.8, assigned to Merck & Co., Inc., and published on Jul. 17, 1991 discloses linear polypeptide fibrinogen receptor antagonists. Eur. Pat. App. No. 90101404.3 discloses compounds of the structure
R$^1$—A—(W)$_a$—X—(CH$_2$)$_b$—(Y)$_c$—B—Z—COOR
wherein R$^1$ is a guanidino or amidino moiety and A and B are chosen from specific monosubstituted aryl or heterocyclic moieties.

The present invention provides novel fibrinogen receptor antagonists that have significant binding activity and are, therefore, useful for the reasons stated herein. A number of very serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

SUMMARY OF THE INVENTION

The invention is a fibrinogen receptor antagonist of the formula:

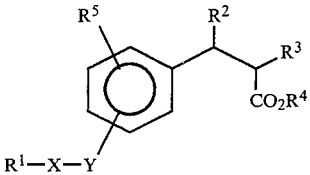

wherein

R$^1$ is a four to eight member heterocyclic ring containing 1, 2, 3 or 4 heteroatoms wherein said heteroatoms are N, O or S and wherein said heterocyclic ring is optionally substituted at any atom by H, R$^6$ or R$^7$;

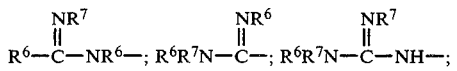

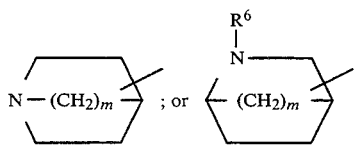

NR$^6$R$^7$ wherein R$^6$ and R$^7$ are independently hydrogen, C$_{1-10}$ alkoxycarbonyl or unsubstituted or substituted C$_{1-10}$ alkyl and cycloalkyl wherein said substituents are
C$_{1-10}$ alkoxy,
C$_{1-10}$ alkoxyalkyl,
C$_{1-10}$ alkoxyalkyloxy,
C$_{1-10}$ alkoxycarbonyl,
C$_{1-10}$ alkylcarbonyl,
C$_{0-6}$ alkylaminocarbonyl,
C$_{1-10}$ aralkylcarbonyl,
aryl C$_{0-6}$ alkyl,
C$_{1-4}$ alkanoylamino,
C$_{1-10}$ alkylsulfonylamino,
C$_{4-10}$ aralkylsulfonylamino,
and further wherein said N can additionally be substituted to form a quaternary ammonium ion wherein said substituent is as previously defined for R$^6$ and R$^7$;

R$^2$ is chosen from:

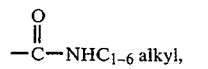

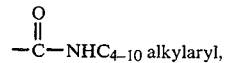

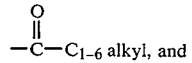

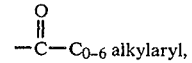

wherein R$^2$ is either unsubstituted or substituted with R$^6$, and

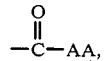

where AA is an L— or D— amino acid or amino acid ester connected through an amide linkage,
R$^3$ is chosen from: hydrogen, C$_{1-10}$ alkyl, (C$_{0-6}$) alkylaryl
(CH$_2$)$_{0-1}$—NHSO$_2$ C$_{1-10}$ alkyl,
(CH$_2$)$_{0-1}$—NHSO$_2$ C$_{0-6}$ alkylaryl,
(CH$_2$)$_{0-1}$—NHSO$_2$NH C$_{0-10}$ alkyl,
(CH$_2$)$_{0-1}$—NHSO$_2$NH C$_{0-6}$ alkylaryl,
(CH$_2$)$_{0-1}$—NHCO C$_{1-10}$ alkyl,
(CH$_2$)$_{0-1}$—NHCO C$_{0-6}$ alkylaryl,
(CH$_2$)$_{0-1}$—NHCO$_2$ C$_{1-10}$ alkyl,
(CH$_2$)$_{0-1}$—NHCO$_2$ C$_{0-6}$ alkylaryl,
(CH$_2$)$_{0-1}$—SO$_2$NH C$_{0-10}$ alkyl,
(CH$_2$)$_{0-1}$—SO$_2$NH C$_{0-6}$ alkylaryl,

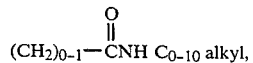

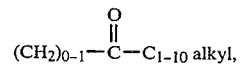

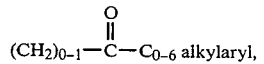

(CH$_2$)$_{0-1}$—NHCONH C$_{0-10}$ alkyl,
(CH$_2$)$_{0-1}$—NHCONH C$_{0-6}$ alkylaryl,
(CH$_2$)$_{0-1}$—SO$_2$ C$_{1-10}$ alkyl,
(CH$_2$)$_{0-1}$—SO$_2$ C$_{0-6}$ alkylaryl,

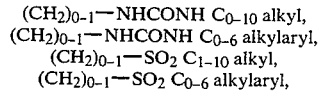

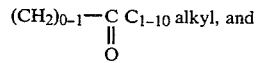

X is chosen from: C$_{1-10}$ alkyl either unsubstituted or substituted with R$^5$ or R$^6$, C$_{4-8}$ cycloalkyl, and aryl;
Y is chosen from: O, S, SO, SO$_2$, —NR$^6$CO—, —CONR$^6$—, —(CH$_2$)$_{0-6}$—,

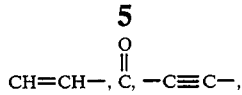

and wherein $(CH_2)_{0-3}$ may be appended at either or both terminii of the above groups;

$R^4$ is chosen from H, $C_{1-4}$ alkyl, and $C_{4-10}$ arylalkyl; and, $R^5$ is chosen from: H, $C_{1-6}$ alkyl, $C_{4-10}$ aryl $C_{0-6}$ alkyl, carboxy$(CH_2)_{0-6}$ alkyl, $C_{1-6}$ alkyloxy, and halogen.

Preferred compounds of the invention have the formula

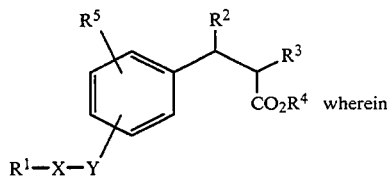

$R^1$ is $NR^6R^7$, wherein $R^6$ and $R^7$ are chosen from hydrogen, $C_{1-6}$ alkyl and $C_{0-6}$ alkylaryl,

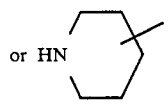

and X, Y, $R^5$, $R^2$ $R^3$ and $R^4$ are as previously defined

More preferred compounds of the invention have the formula,

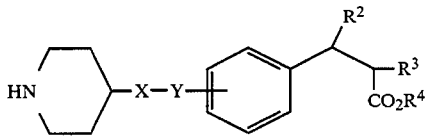

wherein —X—Y— is —$(CH_2)_{2-6}$—O—; $R^2$, $R^3$ and $R^4$ are as previously defined.

DETAILED DESCRIPTION OF THE INVENTION

The term "pharmaceutically acceptable salts" shall mean non-toxic salts of the compounds of this invention which are generally prepared by reacting the free base with a suitable organic or inorganic acid. Representative salts include the following salts: Acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/ diphosphate, polygalacturonate, salicylate, stearate, subacetate, succinate, tannate, tartrate, teoclate, tosylate, triethiodide, valerate.

The term "pharmaceutically effective amount" means that amount of a drug or pharmaceutical agent that will elicit the biological or medical response of a tissue, system or animal that is being sought by a researcher or clinician. The term "anti-coagulant" includes heparin, and warfarin. The term "thrombolytic agent" includes streptokinase and tissue plasminogen activator. The term "platelet anti-aggregation agent" includes aspirin and dipyridamole.

The term "aryl" means a mono- or polycyclic system composed of 5- and 6- membered aromatic rings containing 0,1,2,3, or 4 heteroatoms chosen from N, O or S and either unsubstituted or substituted with $R^4$ or $R^5$.

The term "alkyl" means straight or branched alkane, alkene or alkyne.

The term "alkoxy" includes an alkyl portion where alkyl is as defined above.

The terms "arylalkyl" and "alkylaryl" include an alkyl portion where-alkyl is as defined above and to include an aryl portion where aryl is as defined above. The $C_{0-n}$ or $C_{1-n}$ designation where n may be an integer from 1–10 or 2–10 respectively refers to the alkyl component of the arylalkyl or alkylaryl unit.

The term "halogen" includes fluorine, chlorine, iodine and bromine.

The designation "AA" refers to members of the group of L— or D— amino acids represented by: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine. Under standard nonmenclature used throughout this disclosure, the terminal portion of the designated side chain is described first followed by the adjacent functionallity toward the point of attachment. For example, a $C_{1-6}$ alkyl substituted with $C_{1-6}$alkylcarbonylamino is equivalent to

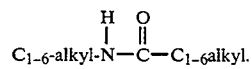

In the schemes and examples below, various reagent symbols have the following meanings:

| | |
|---|---|
| BOC(Boc): | t-butyloxycarbonyl. |
| Pd—C: | Palladium on activated carbon catalyst. |
| DMF: | Dimethylformamide. |
| DMSO: | Dimethylsulfoxide. |
| CBZ: | Carbobenzyloxy. |
| $CH_2Cl_2$: | Methylene chloride. |
| $CHCl_3$: | chloroform. |
| EtOH: | ethanol. |
| MeOH: | methanol. |
| EtOAc: | ethyl acetate. |
| HOAc: | acetic acid. |
| BOP: | Benzotriazol-1-yloxytris(dimethylamino)-phosphonium, hexafluorophosphate. |
| EDC: | 1-(3-Dimethylaminopropyl)-3-ethylcarbodiimide |
| Oxone: | potassium peroxymonosulfate |
| LDA: | Lithium diisopropylamide |
| NMM: | N-Methylmorpholine |

The compounds of the present invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but nontoxic amount of the compound desired can be employed as an anti-aggregation agent.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardivascular surgery where manipulation of arteries and organs, and/or the interaction of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gpIIb/IIIa on the platelet membranes and fibrinogen adsorbed to the surface of the circuit. (Gluszko et al., *Amer. J. Physiol.*, 252(H), 615–621 (1987)). Platelets released from artificial surfaces show impaired hemostatic function. Compounds of the invention may be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty of coronary and other arteries and after coronary artery bypass procedures. They may also be used to prevent myocardial infarction.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarilly skilled physician or veterinarian can readily determine and prescribe the effective amount of the drug required to prevent, counter, or arrest the progress of the condition.

Oral dosages of the present invention, when used for the indicated effects, will range between about 0.01 mg per kg of body weight per day (mg/kg/day) to about 100 mg/kg/day and preferably 1.0–100 mg/kg/day and most preferably 1–20 mg/kg/day. Intravenously, the most preferred doses will range from about 1 to about 10 μg/kg/minute during a constant rate infusion. Advantageously, compounds of the present invention may be administered in divided doses of two, three, or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittant throughout the dosage regime.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with conventional pharmaceutical practices.

For instance, for oral administration in the form of a tablet or capsule, the active drug component can be combined with an oral, non-toxic, pharmaceutically acceptable, inert carier such as lactose, starch, sucrose, glucose, methyl cellulose, magnesium sterate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium sterate, magnesium sterate, sodium benzoate, sodium acetate, sodium chloride and the like. Disintegrators include, without limitation, starch methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinlypyrrolidone, pyran copolymer, polyhydroxypropyl-methacrylamide-phenol, polyhydroxyethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The compounds of the present invention can also be co-administered with suitable anti-coagulation agents or thrombolytic agents such as plasminogen activators or streptokinase to achieve synergystic effects in the treatment of various vascular pathologies. They may also be combined with heparin, aspirin, or warfarin.

The novel compounds of the present invention were prepared according to the procedure of the following schemes and examples, using appropriate materials and are further exemplified by the following specific examples. The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celcius unless otherwise noted.

In addition to the following preparative procedures, several examples of in-vitro bioactivity of compounds within the scope of the present invention are indicated. To illustrate, one test which is used to evaluate fibrinogen receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay used to determine inhibition associated with the compounds claimed in the instant invention, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

Platelet aggregation is measured at 37° C. in a Chronolog aggregometer. The reaction mixture contains gel-filtered human platelets ($2 \times 10^8$ per ml), fibrinogen (100 micrograms per ml (ug/ml)), $Ca^{2+}$(lmM), and the compound to be tested. The aggregation is initiated by adding $10 \mu M$ ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

Scheme 1 outlines a procedure for preparing exemplary compounds of the present invention. Procedures for preparing alternative compounds within the scope of the present invention would be obvious to persons skilled in the art, in view of the process strategy described in Scheme 1.

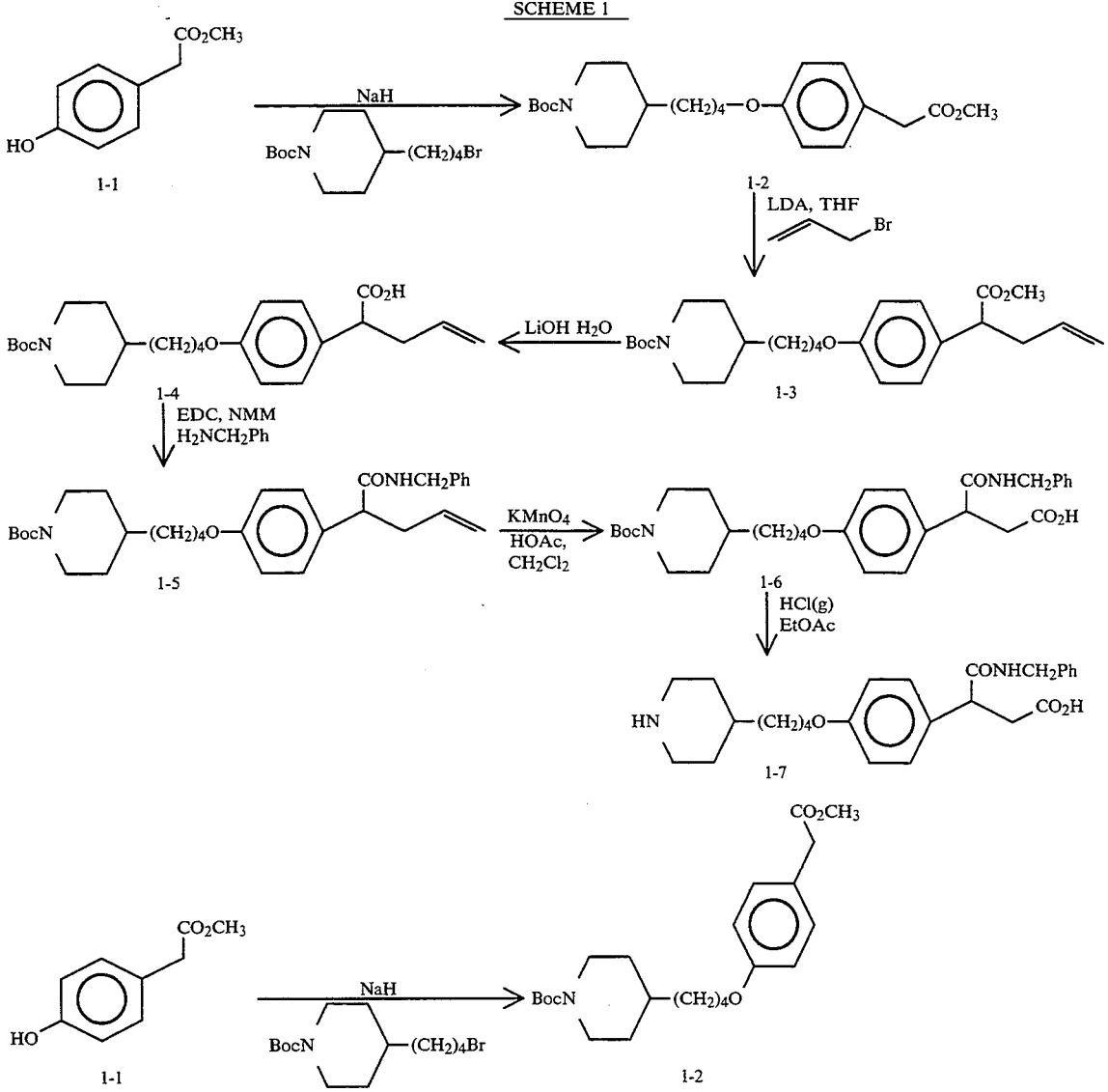

SCHEME 1

Methyl 4-[4-(N-t-Butyloxycarbonylpiperidin-4-yl)butyloxyl-phenylacetate (1-2)

A solution of 1-1 (2.61 g, 0.017 moles) and (N-Boc-4-piperidin-4-yl)butyl bromide (European Publication 478,363) in DMF (65 ml) was cooled at 0°–5° C. and treated with NaH (0.48 g, 0.020 moles) in one portion. The resulting mixture was stirred at 0° for 1 hr. and then for 16 hrs at room temperature.

The solvent was removed (<30°) and the residue was taken up in H₂O (75 ml) and extracted with Et₂O. This ether extract was washed with brine, dried (Na₂SO₄) and the solvent was removed. The resulting residue was purified by flash chromatography on silica gel eluting with 15% EtOAc/hexane to give pure 1-2 as an oil.

¹H NMR (300 MHz, CDCl₃) δ 1.10 (2H, m), 1.32 (4H, m), 1.48 (9H, s), 1.60-1.84 (5H, m), 2.67 (2H, m), 3.55 (2H, s), 3.68 (3H, s), 3.92 (2H, m), 4.09 (2H, m), 6.95 (2H, d), 7.18 (2H, d).

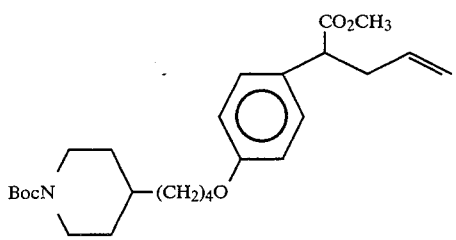

Methyl 4-[4-(N-t-Butyloxycarbonylpiperidin-4-yl)-butyloxyl-2-(3-propenyl)phenylacetate (1-3)

1-2 (8.1 g, 0.020 moles) was added at −70° C. to a THF solution (150 ml) of lithum diisopropylamide prepared at 0° from diisopropylamine (4.05 g, 0.04 moles) and butyllithium. The resulting clear yellow solution of the ester was stirred at −70° for 1 hour and then a solution of allyl bromide (3.62 g, 0.03 moles) in THF (5 ml) was added dropwise. The resulting reaction mixture was stirred at −70° for 1 hr. and then at room temperature for 8 hrs. The reaction was quenched with 10% KHSO₄ solution (5 ml) and the solvent was removed. The residue was taken up in Et₂O (600 ml) and washed with H₂O (100 ml). 10% KHSO₄ solution, brine and dried (Na₂SO₄). The solvent was removed and the residue was purified by flash chromatography on silica gel eluting with 15% EtOAc/hexane to give pure 1-3 as an oil.

¹H NMR (300 MHz. CDCl₃) δ 1.04(2H, m), 1.32 (3H, m), 1.46 (9H, s), 1.65 (2H, d), 1.77 (2H, d), 2.49 (1H, m), 2.48 (2H, t), 2.78 (1H, m), 3.56 (2H, m), 3.65 (3H, s), 3.93 (3H, t), 4.10 (2H, m), 5.02 (2H, m), 5.70 (1H, m), 6.82 (2H, d) 7.02 (2H, d).

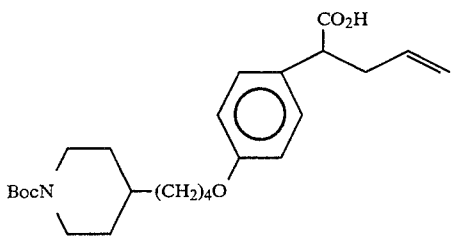

4-[4-N-t-Butyloxycarbonylpiperdidin-4-yl)butyloxy)-2-(3-propenyl)phenylacetic acid (1-4)

A solution of 1-3 (3.2 g, 0.007 moles) in THF(1)/MeOH(1)/H₂O(1) (90 ml) was treated with LiOH•H₂O (0.944 g, 0.022 moles) at room temperature with stirring for 16 hours. The reaction mixture was concentrated to a volume of 30 ml and this was diluted with 170 ml H₂O and acidified to pH 2-3 with 10% KHSO₄ solution. This was extracted with EtOAc and this extract was washed with H₂O brine and dried (Na₂SO₄). Solvent removal gave 1-4 as a viscous oil ¹H NMR (300 MHz, CDCl₃) δ 1.03 (2H, m), 1.28 (3H, m), 1.48 (9H, s), 1.63 (2H, d), 1.75 (2H, m), 2.50 (1H, m), 2.65 (2H, t), 2.79 (1H, m), 3.58 (1H, m), 3.92 (2H, t), 4.05 (2H, m), 5.02 (2H, m), 5.70 (1H, m), 6.83 (2H, d), 7.20 (2H, d).

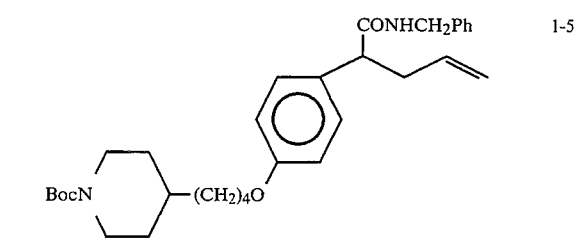

4-[4-N-t-Butyloxycarbonylpiperidin-4-yl )butyloxy]-2-(3-propenyl)phenylacetic acid, N-benzylamide (1-5)

A solution of 1-4 (1.51 g, 0.0035 moles) in DMF (25 ml) was treated with benzylamine (0.407 g, 0.0038 moles) and HOBT (0.54 g, 0.004 moles). This solvent was cooled to 0°-5°, N-methylmorpholine (0.708 g, 0.007 moles) was added, followed by EDC (0.786 g, 0.0041 moles), and the resulting solution was stirred at 0° for 1 hr and then at room temperature for 16 hrs.

The solvent was then removed in vacuo and the residue taken up in H₂O (100 ml) and extracted with EtOAc. The EtOAc extract ,was washed with 10% KHSO₄ solution, H₂O, saturated NaHCO₃ solution, brine, and dried (Na₂SO₄). Solvent removal gave a residue that was purified by flash chromatography on silica gel eluting with hexane (7) −EtOAc (3) to give 1-5 as a viscous residue. R_f 0.35.

¹H NMR (300 MHz, CDCl₃) δ 1.04 (2H, m), 1.36-1.44 (3H, m), 1.47 (9H, s), 1.65 (2H, d), 1.74 (2H, m), 2.52 (1H, m), 2.67 (2H, t), 2.93 (1H, m), 3.39 (1H, t), 3.92 (1H, t), 4.08 (2H, m), 4.40 (2H, m), 5.00 (2H, m), 5.68 (2H, m), 6.84 (2H, d), 7.13-7.32 (7H, m).

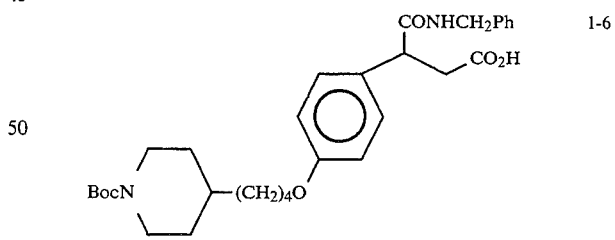

3- [4-(4-N-t-Butyloxycarbonylpiperidin-4-yl )butyloxyphenyl ]-3-(benzylaminocarbonyl )propanoic acid (1-6)

To a solution of KMnO₄ (0.316 g, 0.002 moles) in H₂O (3 ml) cooled to 0-5° was added a solution of 1-5 (0.26 g, 0.0005 moles) in CH₂Cl₂ (3 ml) followed by acetic acid (0.5 ml) and Aliquat-336 (2 drops). The resulting mixture was vigorously stirred in an ice bath for 5 hrs. and then quenched by the addition of 1 g of Na₂SO₃. This was acidified with 10% KHSO₄ solution, diluted with 50 ml H₂O and extracted with CH₂Cl₂. The CH₂Cl₂ extract was washed with brine, dried (Na₂-

SO4) and the solvent removed. The resulting residue was purified by flash chromatography on silica gel eluting with CHCl3(97)/MeOH(3)/HOAc(1) to give pure 1-6, $R_f$ 0.3.

$^1$H NMR (300 MHz, CDCl3) δ 1.04 (2H, m), 1.23–1.30 (3H, m), 1.45 (9H, s), 1.66 (2H, d), 1.75 (2H, m), 2.58–2.75 (3H, m), 3.30 (1H, m), 3.90 (3H, m), 4.06 (2H, m), 4.29–4.50 (2H, m), 5.87 (1H, t), 6.82 (2H, d), 7.10–7.33 (7H, m).

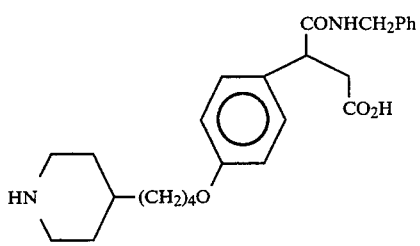

3-[4-(4-Piperidin-4-yl)butyloxyphenyl]-3-(benzylaminocarbonyl)propanoic acid hydrochloride (1-7)

1-6 (0.11 g) was dissolved in EtOAc (30 ml), cooled to −25° C. and treated with HC$_1$ gas for 30 minutes. The reaction flask was then stopped and the reaction mixture was stirred at 0° for 1 hr. The solvent was removed at <10° and the resulting residue was triturated with Et2O to provide 1-7 as a white solid.

$^1$H NMR (300 MHz, CD3OD) δ 1.37 (4H, m), 1.45–1.70 (3H, m), 1.77 (2H, m), 1.95 (2H, m), 2.60 (1H, dd), 2.94 (2H, dt), 3.13 (1H, m), 3.18–3.40 (4H, m), 3.95 (3H, m), 4.31 (2H, m), 6.93 (2H, d), 7.11–7.28 (7H, m).

Analysis Calcd. for $C_{26}H_{34}N_2O_4 \cdot HCl \cdot \frac{1}{2} H_2O$: C, 64,51; H, 7.50; N, 5.79.

Found: C, 64.33; H, 7.48; N, 5.94.

In a similar fashion to that described for 1-7, the following compounds can be prepared:

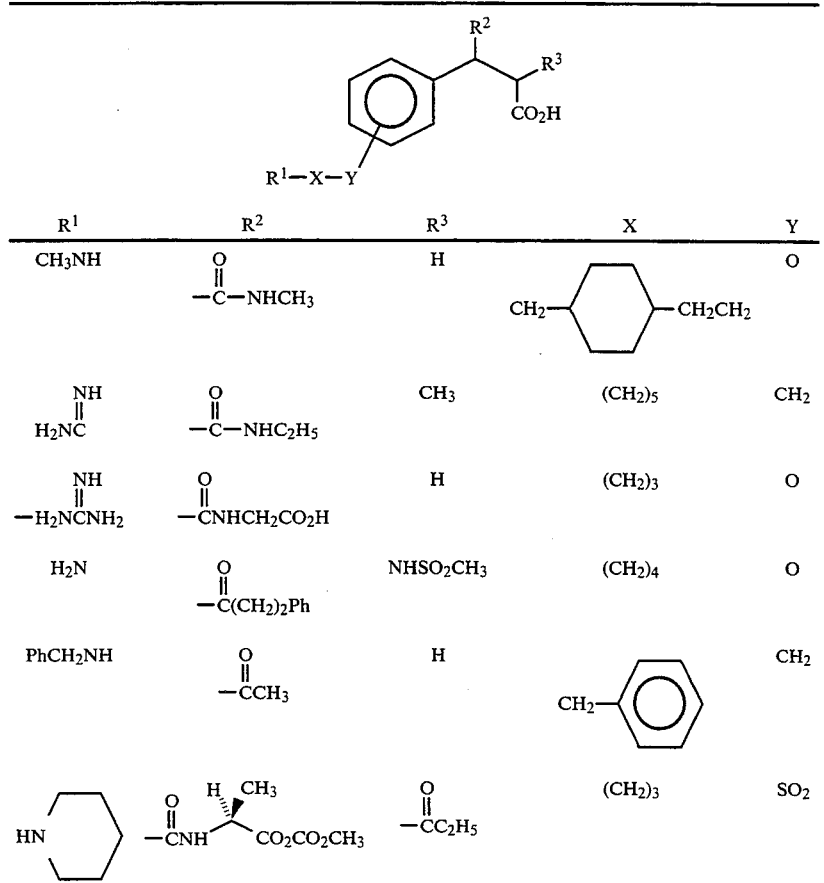

EXAMPLE 2

In Vitro Activity

The test procedures employed to measure the antiplatelet aggregating activity of the compounds of the present invention are described below.

Blood was drawn into 0.1 ml volumes of acid citrate-dextrose (85 mM sodium citrate, 64 mM citric acid, 110 mM dextrose) by venipuncture from normal human volunteers. Platelet-rich plasma was prepared by centrifugation at 400×g for 12 minutes. PGE1 (5mg/ml) was added and platelets were collected by centrifugation at 800×g for 12 minutes. The platelet pellet was resuspended into human platelet buffer (140 mM NaCl 7.9 mM KCl 3.3 mM Na2HPO4, 6 mM HEPES, 2% bovine serum albumin, 0.1% dextrose, pH 7.2) and filtered over Sepharose 2B that was previously equilibrated in human platelet buffer. Human fibrinogen (10–100 mg/ml) and Ca Cl2 (lmM) were added and aggregation was initiated by the addition of 10 mM ADP. Aggregation was monitored by the initial rate of increase of light transmittance.

Therapeutic Treatment

Compounds of the invention may be used for inhibiting integrin protein-complex function relating to cell attachment activity. They may be administered to patients where inhibition of human or mammalian platelet aggregation or adhesion is desired.

Compounds of the invention are particularly useful in inhibiting platelet aggregation in situations where a strong antithrombotic of short duration or effectiveness is needed. Thus, they may find utility in surgery on peripheral arteries (arterial grafts, carotid endaterectomy) and in cardiovascular surgery where manipulation of arteries and organs, and/or the interation of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

Extracorporeal circulation is routinely used for cardiovascular surgery in order to oxygenate blood. Platelets adhere to surfaces of the extracorporael circuit. Adhesion is dependent on the interaction between gpIIb/IIIa on the platelet membranes and fibrinogen adsorbed to the surface of the circuit. (Lluszko et al., Amer. J. Physiol., 252:H, 615–621 (1987). Platelets released from artificial surfaces show impaired hemostatic function. Compounds of the invention may be administered to prevent adhesion.

Other applications of these compounds include prevention of platelet thrombosis, thromboembolism and reocclusion during and after thromboembolytic therapy and prevention of platelet thrombosis, thromboembolism and reocclusion after angioplasty of coronary and other arteries and after coronary artery bypass procedures. Compounds of the invention may also be used to prevent myocardial infarction.

These compounds may be administered by any convenient means which will result in its delivery into the blood stream in substantial amount including continuous intravenous or bolus injection or oral methods. Compositions of the invention include compounds of the invention and pharmaceutically acceptable carriers, e.g. saline, at a pH level of for example 7.4, suitable for achieving inhibition of platelet aggregation. They may also be used in combination with anticoagulants such as heparin or warfarin.

In one exemplary application, a suitable amount of compound is intravenously administered to a heart attack victim undergoing angioplasty. Administration occurs during or several minutes prior to angioplasty, and is in an amount sufficient to inhibit platelet aggregation, e.g. an amount which achieves a steady state plasma concentration of between about 0.01–30uM, preferably between about 0.03–3 uM. When this amount is achieved, an infusion of between about 0.1–100 g per kilo per min., preferably between about 1–20 μg per kilo per min. is maintained to inhibit platelet aggregation. Should the patient need to undergo bypass surgery, administration may be stopped immediately. Under these conditions the fibrinogen receptor antagonists will not cause complications during surgery, as compared to other therapies such as aspirin or monoclonal antibodies, the effects of which last hours after cessation of administration.

The present invention also includes a pharmaceutical composition comprising compounds of the present invention and tissue type plasminogen activitor or streptokinase. The invention also includes a method for promoting thrombolysis and preventing reocclusion in a patient which comprises administering to the patient an effective amount of compositions of the invention.

The present invention may be embodied in other specific forms without departing from the spirt or essential attributes thereof. Thus, the specific examples described above should not be interpreted as limiting the scope of the present invention.

While the invention has been described and illustrated in reference to certain preferred embodients thereof, those skilled in the art will appreciate that various changes, modification and substitutions can be made therein without departing from the spirt and the scope of the invention. For example, effective dosages other than the preferred doses as set fourth hereinabove may be applicable as a consequence of variations in the responsiveness of the mammal being treating for severity of clotting disorders or emboli, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be intepreted as broadly as is reasonable.

What is claimed is:

1. A compound of the formula:

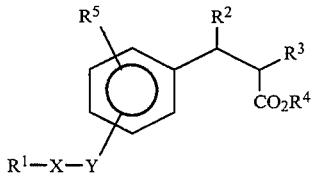

wherein
$R^1$ is

$R^2$ is chosen from

wherein alkyl is either unsubstituted or substituted with $R^6$,

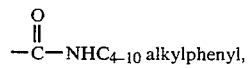

wherein phenyl is either unsubstituted or substituted with $R^6$,

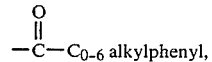

-continued wherein phenyl is either unsubstituted
or substituted with $R^6$, $$-\overset{O}{\underset{\|}{C}}-C_{0-6}\text{ alkylphenyl,}$$

and $$-\overset{O}{\underset{\|}{C}}-AA,$$

where AA is an L- or D- amino acid or amino acid ester
connected through an amide linkage;

$R^3$ is chosen from
hydrogen, $C_{1-10}$ alkyl, $(C_{0-6})$ alkylphenyl,
$(CH_2)_{0-1}$—$NHSO_2C_{1-10}$ alkyl,
$(CH_2)_{0-1}$—$NHSO_2C_{0-6}$ alkylphenyl,
$(CH_2)_{0-1}$—$NHSO_2NH$ $C_{0-10}$ alkyl,
$(CH_2)_{0-1}$—$NHSO_2NH$ $C_{0-6}$ alkylphenyl,
$(CH_2)_{0-1}$—$NHSO$ $C_{1-10}$ alkyl,
$(CH_2)_{0-1}$—$NHSO$ $C_{0-6}$ alkylphenyl,
$(CH_2)_{0-1}$—$NHSO_2$ $C_{1-10}$ alkyl,
$(CH_2)_{0-1}$—$NHSO_2$ $C_{0-6}$ alkylphenyl,
$(CH_2)_{0-1}$—$SO_2NH$ $C_{0-10}$ alkyl,
$(CH_2)_{0-1}$—$SO_2NH$ $C_{0-6}$ alkylphenyl, $$(CH_2)_{0-1}-\overset{O}{\underset{\|}{C}}NH\ C_{0-10}\text{ alkyl,}$$

$$(CH_2)_{0-1}-\overset{O}{\underset{\|}{C}}NH\ C_{0-6}\text{ alkylphenyl,}$$

$$(CH_2)_{0-1}-\overset{O}{\underset{\|}{C}}-C_{1-10}\text{ alkyl,}$$

$$(CH_2)_{0-1}-\overset{O}{\underset{\|}{C}}-C_{0-6}\text{ alkylphenyl,}$$

$(CH_2)_{0-1}$—NHCONH $C_{0-10}$ alkyl,
$(CH_2)_{0-1}$—NHCONH $C_{0-6}$ alkylphenyl,
$(CH_2)_{0-1}$—$SO_2$ $C_{1-10}$ alkyl,
$(CH_2)_{0-1}$—$SO_2$ $C_{0-6}$ alkylphenyl, $$(CH_2)_{0-1}-\underset{\underset{O}{\|}}{C}\ C_{1-10}\text{ alkyl,}$$

and $$(CH_2)_{0-1}-\underset{\underset{O}{\|}}{C}\ C_{0-6}\text{ alkylphenyl;}$$

X is chosen from $C_{1-10}$ alkyl either unsubstituted or substituted with $R^5$ or $R^6$;
Y is chosen from O, S, SO, and $SO_2$;
$R^4$ is chosen from H, $C_{1-4}$ alkyl, and $C_{0-6}$ alkyl;
$R^5$ is chosen from H, $C_{1-6}$ alkyl, $C_{0-6}$ alkyl, carboxy $(CH_2)_{0-6}$ alkyl, $C_{1-6}$ alkyloxy, and halogen; and
$R^6$ is hydrogen, $C_{1-10}$ alkoxycarbonyl or unsubstituted or substituted $C_{1-10}$ alkyl wherein said substituents are
$C_{1-10}$ alkoxy,
$C_{1-10}$ alkoxyalkyl,
$C_{1-10}$ alkoxyalkyloxy,
$C_{1-10}$ alkoxycarbonyl,
$C_{1-10}$ alkylcarbonyl, $C_{0-6}$ alkylaminocarbonyl,
phenyl $C_{0-6}$ alkylcarbonyl, phenyl $C_{0-6}$ alkyl,
$C_{1-4}$ alkanoylamino,
$C_{1-10}$ alkylsulfonylamino, or
phenyl $C_{0-6}$ alkylsulfonylamino.

2. A compound according to claim 1 wherein —X—Y—is —$(CH_2)_{2-6}O$—;
$R^5$ is H;
$R^2$ is chosen from $$-\overset{O}{\underset{\|}{C}}-NHC_{1-6}\text{ alkyl,}$$

wherein alkyl is either unsubstituted
or substituted with $R^6$, $$-\overset{O}{\underset{\|}{C}}-NHC_{4-10}\text{ alkylphenyl,}$$

wherein phenyl is either unsubstituted
or substituted with $R^6$, $$-\overset{O}{\underset{\|}{C}}-C_{0-6}\text{ alkylphenyl,}$$

wherein phenyl is either unsubstituted
or substituted with $R^6$, $$-\overset{O}{\underset{\|}{C}}-C_{0-6}\text{ alkylphenyl,}$$

and $$-\overset{O}{\underset{\|}{C}}-AA,$$

where AA is an L- or D- amino acid or amino acid ester
connected through an amide linkage;

$R^3$ is chosen from
hydrogen, $C_{1-10}$ alkyl, $(C_{0-6})$ alkylphenyl,
$(CH_2)_{0-1}$—$NHSO_2$ $C_{1-10}$ alkyl,
$(CH_2)_{0-1}$—$NHSO_2$ $C_{0-6}$ alkylphenyl,
$(CH_2)_{0-1}$—$NHSO_2NH$ $C_{0-10}$ alkyl,
$(CH_2)_{0-1}$—$NHSO_2NH$ $C_{0-6}$ alkylphenyl,
$(CH_2)_{0-1}$—NHCO $C_{1-10}$ alkyl,
$(CH_2)_{0-1}$—NHCO $C_{0-6}$ alkylphenyl,
$(CH_2)_{0-1}$—$NHCO_2$ $C_{1-10}$ alkyl,
$(CH_2)_{0-1}$—$NHCO_2$ $C_{0-6}$ alkylphenyl,
$(CH_2)_{0-1}$—$SO_2NH$ $C_{0-10}$ alkyl,
$(CH_2)_{0-1}$—$SO_2NH$ $C_{0-6}$ alkylphenyl, $$(CH_2)_{0-1}-\overset{O}{\underset{\|}{C}}NH\ C_{0-10}\text{ alkyl,}$$

$$(CH_2)_{0-1}-\overset{O}{\underset{\|}{C}}NH\ C_{0-6}\text{ alkylphenyl,}$$

$$(CH_2)_{0-1}-\overset{O}{\underset{\|}{C}}-C_{1-10}\text{ alkyl,}$$

$$(CH_2)_{0-1}-\overset{O}{\underset{\|}{C}}-C_{0-6}\text{ alkylphenyl,}$$

$(CH_2)_{0-1}$—NHCONH $C_{0-10}$ alkyl,
$(CH_2)_{0-1}$—NHCONH $C_{0-6}$ alkylphenyl,
$(CH_2)_{0-1}$—$SO_2$ $C_{1-10}$ alkyl,
$(CH_2)_{0-1}$—$SO_2$ $C_{0-6}$ alkylphenyl, -continued $(CH_2)_{0-1}-\underset{\underset{O}{\|}}{C}\, C_{1-10}$ alkyl, and $(CH_2)_{0-1}-\underset{\underset{O}{\|}}{C}\, C_{0-6}$ alkylphenyl; and $R^4$ is chosen from H, $C_{1-4}$ alkyl, phenyl $C_{0-6}$ alkyl.

3. A compound according to claim 2 which is:

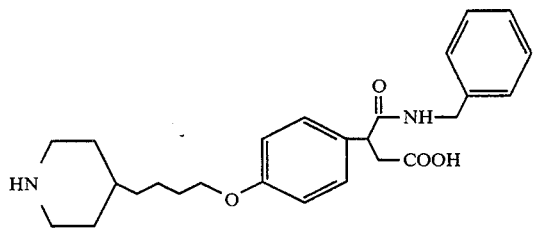

4. A pharmaceutical composition for inhibiting the binding of fibrinogen to blood platelets in a mammal, comprising an antifibrinogenic binding effective amount of a compound of claim 1 and a pharmaceutically acceptable carrier.

5. A method of blocking fibrinogen from acting at its receptor site in a mammal, comprising administering a pharmacologically effective amount of a compound as claimed in claim 1.

6. A method of preventing thrombus and embolus formation in a mammal in need thereof, by blocking fibrinogen from acting at its receptor site, comprising administering an antifibrinogenic binding effective amount of a compound as claimed in claim 1.

7. A method of treating thrombus and embolus formation in a mammal in need thereof, by blocking fibrinogen from acting at its receptor site, comprising administering an antifibrinogenic binding effective amount of a compound as claimed in claim 1.

8. A method of inhibiting aggregation of blood platelets in a mammal by blocking fibrinogen from acting at its receptor site, comprising administering an antifibrinogenic binding effective amount of a compound as claimed in claim 1.

* * * * *